United States Patent [19]
Brunelle et al.

[11] Patent Number: 6,028,203
[45] Date of Patent: Feb. 22, 2000

[54] PHASE TRANSFER CATALYZED METHOD FOR PREPARED OXYBISPHTHALIC COMPOUNDS

[75] Inventors: Daniel Joseph Brunelle, Burnt Hills, N.Y.; Thomas Link Guggenheim, Mt. Vernon, Ind.

[73] Assignee: General Electric Company, Schenectady, N.Y.

[21] Appl. No.: 09/210,707

[22] Filed: Dec. 14, 1998

[51] Int. Cl.[7] .................. C07D 405/00; C07D 209/02; C07D 209/48; C07D 307/77
[52] U.S. Cl. .................. 548/454; 548/455; 548/461; 549/241
[58] Field of Search .................. 548/454, 456, 548/461, 455; 549/305, 241

[56] References Cited

U.S. PATENT DOCUMENTS

| | | | |
|---|---|---|---|
| 4,808,731 | 2/1989 | Berdahl et al. | 549/241 |
| 4,933,469 | 6/1990 | Berdahl et al. | 548/476 |
| 4,946,985 | 8/1990 | Stults | 549/241 |
| 5,132,423 | 7/1992 | Brunelle et al. | 544/162 |
| 5,153,335 | 10/1992 | Stults | 549/243 |

*Primary Examiner*—Zinna Northington Davis
*Assistant Examiner*—Binta Robinson
*Attorney, Agent, or Firm*—Bruce S. Brown; Noreen C. Johnson

[57] ABSTRACT

Oxybisphthalic compounds such as 4,4'-oxybis(N-methylphthalimide) and 4,4'-oxybis(phthalic anhydride) are prepared from the corresponding nitro- or halo-substituted phthalic compounds by reaction with an alkanoate or carbonate salt in a non-polar solvent and in the presence of a hexaalkylguanidinium salt as phase transfer catalyst. A carboxylic acid such as 4-chlorobenzoic acid may be used as an additional catalyst. Reaction rates and yields are higher than with other phase transfer catalysts.

23 Claims, No Drawings

PHASE TRANSFER CATALYZED METHOD FOR PREPARED OXYBISPHTHALIC COMPOUNDS

BACKGROUND OF THE INVENTION

This invention relates to the preparation of oxybisphthalic compounds, and more particularly to their preparation by an improved phase transfer catalysis method.

Oxybisphthalimides and oxybis(phthalic anhydrides) are intermediates for the preparation of polyetherimides. The oxybisphthalimides have, in some instances, been easier to prepare than the oxybis(phthalic anhydrides) and can subsequently be converted thereto by hydrolysis and dehydration. It is also possible, however, to prepare oxybis(phthalic anhydrides) directly.

As disclosed in U.S. Pat. No. 4,780,544, the oxybisphthalimides have been prepared by the reaction of a nitro-substituted phthalimide with an alkali metal carboxylate such as potassium acetate in a dipolar aprotic solvent such as dimethylformamide or dimethyl sulfoxide. More conveniently, U.S. Pat. No. 4,933,469 describes their preparation in a non-polar organic solvent, preferably in the presence of a phase transfer catalyst. Reaction temperatures are in the range of about 100–4000°C., most often about 150–200° C. Yields above 70% are obtained with a dialkylaminopyridinium salt as phase transfer catalyst only when the solvent is distilled through calcium hydride to remove water; similar yields can also be obtained by the catalytic use of tetraphenylphosphonium bromide, a very expensive compound. U.S. Pat. No. 4,808,731 discloses the preparation of oxybis(phthalic anhydrides) by a simple condensation of a nitro- or fluoro-substituted phthalic anhydride (not requiring carboxylate), also in the presence of a dialkylaminopyridine, but disclosed yields are no higher than 57%.

A method similar to that of the aforementioned patents but using, for example, alkali metal carbonates instead of carboxylates is also known. U.S. Pat. No. 4,946,985 discloses such a method in which the carbonate is used in combination with water. According to U.S. Pat. No. 5,153,335, the reaction is more effectively conducted in the absence of water and employs a benzoic acid such as 4-chlorobenzoic acid as a catalyst.

U.S. Pat. No. 5,132,423 discloses the use of substituted guanidinium salts as phase transfer catalysts for nucleophilic aromatic substitution reactions such as the reaction of bisphenol A salts with halo- or nitro-substituted phthalimides to yield bis(phthalimides). It is not clear therefrom, however, whether the reaction between a substituted phthalic compound and a carboxylate or carbonate salt is chemically similar.

SUMMARY OF THE INVENTION

The present invention is based on the discovery that substituted guanidinium salts can be employed in the preparation of oxybisphthalic compounds in non-polar solvents. When so employed, they afford the desired products in high yield without the need for burdensome solvent drying operations.

The invention is a method for preparing an oxybisphthalic compound of the formula

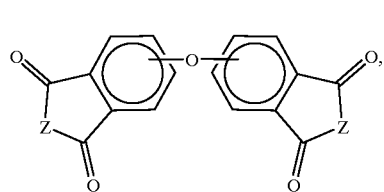

wherein Z is O or N—$R^1$ and $R^1$ is $C_{1-8}$ alkyl, which comprises contacting a substituted phthalic compound of the formula

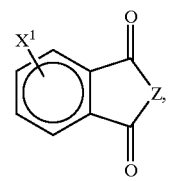

wherein $X^1$ is halo or nitro, with at least one carboxylate of the formula

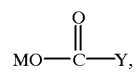

wherein Y is $C_{1-8}$ alkyl, OM or OH and M is an alkali metal, in a substantially non-polar solvent and in the presence of at least one phase transfer catalyst, said catalyst being a guanidinium salt of the formula

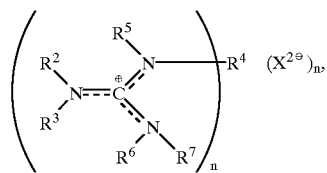

wherein:
each of $R^2 R^3$, $R^5$, $R^6$ and $R^7$ is a primary alkyl radical and $R^4$ is a primary alkyl or primary alkylene radical, or at least one of the $R^2$—$R^3$, $R^4$—$R^5$ and $R^6$—$R^7$ combinations with the connecting nitrogen atom forms a heterocyclic radical;
$X^2$ is an anion; and
n is 1 or 2.

DETAILED DESCRIPTION; PREFERRED EMBODIMENTS

The substituted phthalic compound of formula II may be an anhydride, or an imide in which $R^1$ is an alkyl radical, preferably primary or secondary, containing 1–8 carbon atoms. Methyl radicals are preferred. The $X^1$ substituent may be nitro or halo (especially fluoro, chloro or bromo) and may be in the 3- or, preferably, the 4-position. In many instances, the preferred compounds of formula II are 4-nitro-N-methylphthalimide, the 4-chloro analog and the corresponding anhydrides.

Suitable carboxylates of formula III include alkanoates, in which Y is $C_{1-8}$ alkyl and especially methyl, and carbonates, in which Y is OM or OH. The M value is an alkali metal, preferably sodium or potassium.

Contact between the phthalic compound and the carboxylate is effected in a substantially non-polar solvent. Suitable solvents include aromatic hydrocarbons such as toluene and xylene; chlorinated aromatic hydrocarbons such as chlorobenzene, o-dichlorobenzene and 1,2,4-trichlorobenzene; and ethers and sulfones such as phenyl ether, diphenyl sulfone, and sulfolane. For the most part, solvents having a boiling point of at least about 150° C. are preferred since it is convenient to conduct the reaction under reflux and the use of lower boiling solvents can undesirably prolong reaction time. The preferred solvents are o-dichlorobenzene (ODCB) and 1,2,4-trichlorobenzene, with ODCB generally being most preferred by reason of its availability and relatively low cost.

The alkyl radicals suitable as $R^{2-3}$ and $R^{5-7}$ in the guanidinium salts of formula IV employed as phase transfer catalysts are primary alkyl radicals, generally containing about 1–12 and preferably about 2–6 carbon atoms. Alternatively, any combination of those radicals and the corresponding nitrogen atom(s) may form a heterocyclic radical such as piperidino, pyrrolo or morpholino. $R^4$ is usually an alkyl radical of the same structure as $R^{2-3}$ and $R^{5-7}$, or a $C_{2-12}$ alkylene radical in which the terminal carbons are primary; most preferably, $R^4$ is $C_{2-6}$ alkyl or $C_{4-8}$ straight chain alkylene.

The $X^2$ value may be any anion and is preferably an anion of a strong acid; examples are chloride, bromide and methanesulfonate. Chloride and bromide ions are usually preferred. The value of n will be 1 or 2 depending on whether $R^4$ is alkyl or alkylene.

As indicated by the dotted bonds in formula IV, the positive charge in the guanidinium salt is delocalized over one carbon and 3 nitrogen atoms. This is believed to contribute to the salt's stability under the conditions encountered according to the invention, which may include relatively high temperatures.

According to the invention, contact between the above-described materials is effected under reaction-promoting conditions, generally including temperatures of at least about 150° C. and preferably in the range of about 150–225° C., and the maintenance of an inert atmosphere such as nitrogen. The molar ratio of carboxylate to substituted phthalic compound is most often at least 1:1 and preferably in the range of about 1.0–1.5:1. Phase transfer catalyst is usually present in the amount of about 1–15 mole percent based on substituted phthalic compound.

As previously mentioned, continuous drying of reagents and/or solvent during the reaction is unnecessary for the purposes of the invention. It is sufficient to dry prior to reaction both the carboxylate and substituted phthalic compound in vacuum, and the solvent by contact with an effective drying agent such as molecular sieves.

One method of producing hexaalkylguanidinium halides, especially chlorides, involves drying of the guanidinium salt by azeotropic distillation of an aqueous brine containing said salt with a liquid such as toluene. When so produced, the guanidinium salt may be accompanied by the inorganic salt constituent of the brine, most often sodium chloride. This is not in any way detrimental to the performance of the guanidinium salt as a phase transfer catalyst according to the invention.

It is within the scope of the invention to employ additional catalysts, as previously noted, in combination with the phase transfer catalysts. Suitable other catalysts, which may be effective to further increase yield, include carboxylic acids such as 4-chlorobenzoic acid. When used, the other catalyst may be present in the amount of about 1–10 mole percent based on substituted phthalic compound.

The course of the reaction between carboxylate and substituted phthalic compound may be followed by removing samples, quenching them with an acidic reagent such as acetic acid, diluting with a suitable organic liquid such as acetonitrile and analyzing for reactants and product by high pressure liquid chromatography. Isolation of product from the reaction mixture may be achieved by conventional means, typically by cooling, separation of the oxybisphthalic compound as a solid, washing and drying.

The method of the invention is illustrated by the following examples, all conducted in a nitrogen atmosphere. Potassium acetate and potassium carbonate were previously dried under vacuum at 150° C., substituted phthalimides and phthalic anhydrides at 50° C. and guanidinium salts at 100° C. (unless otherwise specified). Solvents were dried by contact with activated 4A molecular sieves.

EXAMPLES 1–2

Each of a pair of 50-ml 3-necked flasks fitted with stirrers and nitrogen supply means was charged with 4.90 g (50 mmol) of potassium acetate and heated at 180° C. under vacuum for 15 minutes. The vacuum was released with nitrogen and 10.30 g (50 mmol) of 4-nitro-N-methylphthalimide and 25 ml of ODCB were added. Hexaethylguanidinium chloride (HEGCl) or hexa-n-propylguanidinium chloride (HPGCl), 10 mole percent based on substituted phthalimide, was added carefully so as to avoid a vigorous exotherm, as a solution in 3 ml of ODCB. The mixture turned dark brown as a result of the evolution of nitrogen oxides. Samples were periodically taken and analyzed for remaining substituted phthalimide. The product was the desired 4,4'-oxybis(N-methylphthalimide).

The results are given in Table I. Comparison is made with Control 1, employing N-(2-ethylhexyl) 4-dimethylaminopyridinium chloride (EHDMAP) as phase transfer catalyst at the same mole percent level, and Control 2 in which the reaction was conducted in dimethylformamide without the use of a phase transfer catalyst, as disclosed in Example 1 of the aforementioned U.S. Pat. No. 4,780,544.

TABLE I

| | Example | | | |
|---|---|---|---|---|
| | 1 | 2 | Control 1 | Control 2 |
| | | Catalyst | | |
| | HEGCl | HEGCl | EHDMAP | — |
| Time, hrs. | Substituted phthalimide remaining, % | | | |
| 0.25 | 70 | 71.2 | 81.7 | 82 |
| 1 | 37 | — | 65 | 75.4 |
| 2 | — | 41.8 | — | 63.3 |
| 3 | 0 | 25.9 | 36 | — |
| 4 | — | — | — | 46.9 |
| 6 | — | 0 | — | 43.3 |

The improvement in reaction rate afforded by the invention, in comparison to both the use of the aminopyridine as phase transfer catalyst and the use of a dipolar aprotic solvent without phase transfer catalyst, is apparent.

EXAMPLE 3

The procedure of Examples 1–2 was repeated, except that 5 mole percent of HEGCl was employed, the solvent was 1,2,4-trichlorobenzene and the reaction temperature was 215° C. The results are given in Table II, in comparison with Control 3 in which an equal mole percent of tetraphenylphosphonium chloride (TPPC) was employed as phase transfer catalyst.

TABLE II

| Time, hrs. | Example | |
|---|---|---|
| | Ex. 3 | Control 3 |
| | Catalyst | |
| | HEGCl | TPPC |
| | Substituted phthalimide remaining, % | |
| 0.5 | 50.4 | 94.6 |
| 1 | 45.2 | 94.2 |
| 2 | 35.9 | 93.8 |
| Final yield, % | 60.9 | 6.2 |

These results demonstrate the superiority of the hexaalkylguanidinium salts in terms of increased reaction rate.

EXAMPLE 4

The procedure of Example 3 was repeated, substituting potassium carbonate on an equimolar basis for the potassium acetate. The results are given in Table III.

TABLE III

| Time, hrs. | Example | |
|---|---|---|
| | Ex. 4 | Control 4 |
| | Catalyst | |
| | HEGCl | TPPC |
| | Substituted phthalimide remaining, % | |
| 0.5 | 74 | 98 |
| 1 | 44 | 98 |
| 2 | 23.2 | 99 |
| 4 | 13.8 | 96 |
| Final yield, % | 69 | 1.7 |

These results are consistent with those of Example 3 and show that alkali metal carbonates, in the substantial absence of water, are also effective reagents for the preparation of oxybisphthalic compounds according to this invention.

EXAMPLE 5

The procedure of Example 4 was repeated with the addition of 5% based on substituted phthalimide, of 4-chlorobenzoic acid as additional catalyst. The results are given in Table IV.

TABLE IV

| Time, hrs. | Example | |
|---|---|---|
| | Ex. 5 | Control 5 |
| | Catalyst | |
| | HEGCl | TPPC |
| | Substituted phthalimide remaining, % | |
| 0.5 | 85 | 96 |
| 1 | 76 | 96 |
| 2 | 54.9 | 95.3 |
| 4 | 40.3 | 95 |
| 6 | 36.4 | 92.5 |
| Final yield, % | 59 | 5.2 |

EXAMPLE 6

The procedure of Example 4 was repeated, substituting 4-chloro-N-methylphthalimide on an equimolar basis for the nitrophthalimide and employing HEGCl at 1 mole percent. The results are given in Table V, in comparison with a control in which TPPC was employed at 0.5 percent.

TABLE V

| Time, hrs. | Example | |
|---|---|---|
| | Ex. 6 | Control 6 |
| | Catalyst | |
| | HEGCl | TPPC |
| | Substituted phthalimide remaining, % | |
| 1 | 79.6 | 40 |
| 2 | 53.5 | 32.8 |
| 3 | 33.2 | 26.3 |
| Final yield, % | 69.3 | 64.5 |

The results of Examples 5–6 are consistent with those of previous examples.

EXAMPLE 7

A first 2-l oil-jacketed reactor with a bottom valve was equipped with a mechanical stirrer, Dean-Stark trap topped with a reflux condenser, and nitrogen supply means. It was charged with 260.8 g (1.265 moles) of 4-nitro-N-methylphthalimide, 473 ml of ODCB and 25 g (95 mmol) of HEGCl (dried from a brine solution as described hereinabove). The solution was heated to reflux and 100 ml of ODCB was removed with a nitrogen sweep.

A second, similarly equipped 2-l oil-jacketed reactor was placed under the first reactor and charged with 124 g (1.265 mole) of potassium acetate and 293 ml of ODCB. This mixture was heated and ODCB removed in the same way.

The contents of the first reactor were transferred over 10 minutes, with stirring, to the second via a transfer tube, with maintenance of the temperature at 1 85° C. Refluxing was observed and colorless oxides of nitrogen evolved; they turned brown upon exposure to air. Heating and stirring were continued for 6 hours, after which the mixture was allowed to cool and solids were removed over 4 hours by suction filtration through a fritted funnel.

The solids so removed were washed twice with 100-ml portions of water and vacuum dried at 140° C., yielding the desired 4,4'-oxybis(N-methylphthalimide) in 71% yield.

EXAMPLE 8

The procedure of Example 7 is repeated, substituting 4-nitrophthalic anhydride on an equimolar basis for the 4-nitro-N-methylphthalimide. The product is the desired 4,4'-oxybis(phthalic anhydride).

What is claimed is:

1. A method for preparing an oxybisphthalic compound of the formula

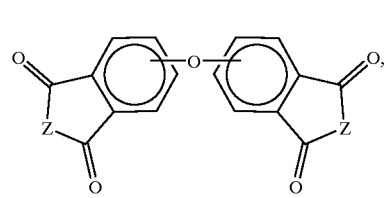

(I)

wherein Z is O or N—$R^1$ and $R^1$ is $C_{1-8}$ alkyl, which comprises contacting a substituted phthalic compound of the formula

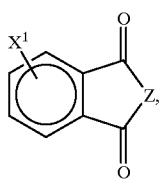
(II)

wherein $X^1$ is halo or nitro, with at least one carboxylate of the formula

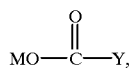
(III)

wherein Y is $C_{1-8}$ alkyl, OM or OH and M is an alkali metal, in a non-polar solvent and in the presence of at least one phase transfer catalyst, said catalyst being a guanidinium salt of the formula

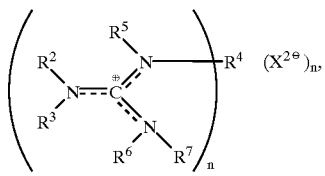
(IV)

wherein:
each of $R^2$, $R^3$, $R^5$, $R^6$ and $R^7$ is a primary alkyl radical and $R^4$ is a primary alkyl or primary alkylene radical, or at least one of the $R^2$—$R^3$, $R^4$—$R^5$ and $R^6$—$R^7$ combinations with the connecting nitrogen atom forms a heterocyclic radical;
$X^2$ is an anion; and
n is 1 or 2.

2. A method according to claim 1 wherein $X^1$ is in the 4-positon.

3. A method according to claim 2 wherein $X^1$ is nitro or chloro.

4. A method according to claim 3 wherein Z is N—$R^1$.

5. A method according to claim 4 wherein $R^1$ is methyl.

6. A method according to claim 3 wherein Z is O.

7. A method according to claim 1 wherein M is sodium or potassium.

8. A method according to claim 7 wherein Y is alkyl.

9. A method according to claim 8 wherein Y is methyl.

10. A method according to claim 7 wherein Y is OM or OH.

11. A method according to claim 1 wherein $X^2$ is selected from the group consisting of chloride, bromide and methanesulfonate.

12. A method according to claim 11 wherein $X^2$ is chloride.

13. A method according to claim 1 wherein the solvent is a chlorinated aromatic hydrocarbon.

14. A method according to claim 13 wherein the solvent is o-dichlorobenzene or 1,2,4-trichlorobenzene.

15. A method according to claim 1 wherein the reaction temperature is at least about 150° C.

16. A method according to claim 1 wherein the molar ratio of carboxylate to substituted phthalic compound is in the range of about 1.0–1.5:1.

17. A method according to claim 1 wherein each of $R^{2-7}$ is ethyl and n is 1.

18. A method according to claim 1 wherein each of $R^{2-7}$ is n-propyl and n is 1.

19. A method according to claim 1 wherein the phase transfer catalyst is present in the amount of about 1–15 mole percent based on substituted phthalic compound.

20. A method according to claim 1 wherein a carboxylic acid is employed as an additional catalyst.

21. A method according to claim 20 wherein the carboxylic acid is 4-chlorobenzoic acid.

22. A method according to claim 20 wherein the carboxylic acid is present in the amount of about 1–10 mole percent based on substituted phthalic compound.

23. A method for preparing an oxybisphthalic compound of the formula

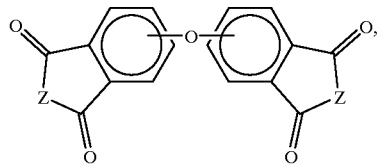

wherein Z is O or N—$CH_3$, which comprises contacting a substituted phthalic compound of the formula

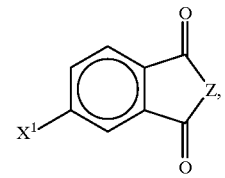

wherein $X^1$ is halo or nitro, with at least one carboxylate of the formula

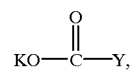

wherein Y is $C_{1-8}$ alkyl, OK or OH, in a non-polar solvent and in the presence of at least one phase transfer catalyst, said catalyst being a guanidinium salt of the formula

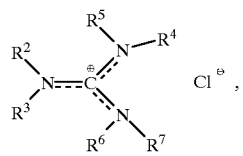

wherein:
each of $R^2$, $R^3$, $R^4$, $R^5$, $R^6$ and $R^7$ is ethyl or n-propyl.

* * * * *